United States Patent [19]

Roth

[11] 4,179,444
[45] Dec. 18, 1979

[54] PROCESS FOR THE MANUFACTURE OF ISO-IMIDES OR MIXTURES OF ISO-IMIDES AND IMIDES

[75] Inventor: Martin Roth, Basel, Switzerland

[73] Assignee: Ciba-Geigy Corporation, Ardsley, N.Y.

[21] Appl. No.: 908,338

[22] Filed: May 22, 1978

Related U.S. Application Data

[63] Continuation of Ser. No. 764,624, Feb. 1, 1977, abandoned.

[30] Foreign Application Priority Data

Feb. 11, 1976 [CH] Switzerland .................... 1648/76

[51] Int. Cl.² ............................................. C07D 403/10
[52] U.S. Cl. ........................... 260/326 N; 260/326.26; 260/326.5 FM; 260/343.3 R; 260/343.6
[58] Field of Search ............... 260/343.6, 343.3 R, 260/326.26, 326.5 FM, 326 N

[56] References Cited

U.S. PATENT DOCUMENTS

| | | | |
|---|---|---|---|
| 2,444,536 | 7/1948 | Searle | 260/326.5 FM |
| 2,980,694 | 4/1961 | Sauers et al. | 260/343.6 |
| 2,980,701 | 4/1961 | Sauers et al. | 260/343.6 |
| 2,995,577 | 8/1961 | Sauers et al. | 260/343.6 |
| 2,998,429 | 8/1961 | Sauers et al. | 260/343.6 |
| 3,023,240 | 2/1962 | Sauers et al. | 260/343.6 |
| 3,035,065 | 5/1962 | Sauers et al. | 260/343.6 |
| 3,041,376 | 6/1962 | Sauers et al. | 260/343.6 |
| 3,179,630 | 4/1965 | Endrey | 260/78 TF |
| 3,472,817 | 10/1969 | Hedaya et al. | 260/343.3 R |
| 3,743,654 | 7/1973 | Fuyinami et al. | 260/326.5 FM |
| 3,839,358 | 10/1974 | Bargain | 260/326.26 |
| 3,975,401 | 8/1976 | Balme | 260/326.26 |
| 3,979,393 | 9/1976 | Kuita et al. | 260/343.3 R |
| 3,985,773 | 10/1976 | Alt et al. | 260/343.3 R |
| 3,990,880 | 11/1976 | Mumford | 260/343.3 R |

OTHER PUBLICATIONS

Adrova et al., Polyimides a New Class of Heat-Resistant Polymers, p. 12 (1969).

*Primary Examiner*—Donald G. Daus
*Assistant Examiner*—Mary Lee
*Attorney, Agent, or Firm*—Luther A. R. Hall

[57] ABSTRACT

A process for the manufacture of iso-imides or mixtures of iso-imides and imides by reacting corresponding amide-acids with ketene at temperatures of about −10° C. to +80° C. is described. According to the process of the invention, the iso-imides or mixtures of iso-imides and imides can be manufactured in a simple, economical manner and in good to very good yields. The acetic anhydride formed during the reaction with the ketene can easily be recovered.

9 Claims, No Drawings

PROCESS FOR THE MANUFACTURE OF ISO-IMIDES OR MIXTURES OF ISO-IMIDES AND IMIDES

This is a continuation of application Ser. No. 764,624, filed on Feb. 1, 1977 now abandoned.

The present invention relates to a process for the manufacture of iso-imides or mixtures of iso-imides and imides.

Various processes for the manufacture of N-substituted isomaleimides and isophthalimides and of N,N'-bis-isomaleimides and N,N'-bis-isophthalimides are known from the literature. Thus, N-substituted maleamic or phthalamic acids and also N,N-bis-maleamic acids or N,N'-bis-phthalamic acids can be converted into the corresponding iso-imides in the presence of various dehydrating agents, such as acetic anhydride, trifluoroacetic anhydride, acetyl chloride, thionyl chloride or dichloroacetyl chloride, preferably with the additional use of a tertiary amine, such as triethylamine, or in the presence of carbodiimides, for example, dicyclohexylcarbodiimide [compare U.S. Pat. Nos. 2,995,577, 2,998,429, 3,035,065 and 3,472,817 and also J. Org. Chem., 28, 2,018–2,024 (1963), 34, 2,275–2,279 (1969) and 36, 821–823 (1971)]. According to U.S. Patent Specification 2,980,701, ammonium salts of N-substituted maleamic acids can also be converted into the corresponding iso-imides in the presence of esters of acid halides, such as ethyl chloroformate.

These known processes are relatively involved and in some cases also require expensive dehydrating agents. Above all, however, with these processes considerable amounts of one or more by-products are obtained, the working up of which, if it is possible at all, is very laborious and costly. Finally, the elimination, in a manner which meets the current regulations for environmental protection, of by-products which cannot be utilised again, for example the elimination of the salts obtained when the reaction is carried out in the presence of acetyl chloride, acetic anhydride or trifluoroacetic anhydride and a tertiary amine, is frequently problematical and extremely expensive.

It has now been found that it is possible, whilst avoiding the abovementioned disadvantages, to manufacture isoimides of the formula

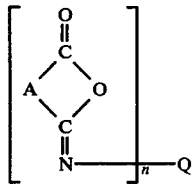

(I)

or mixtures of iso-imides of the formula I and imides of the formula Ia

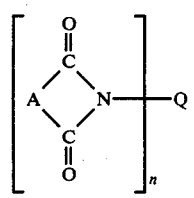

(Ia)

in which A represents —CH=CH— or

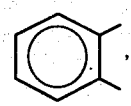

n represents the number 1 or 2 and, when n=1, Q represents an unsubstituted or substituted aryl group, and when n=2, Q represents an unsubstituted or substituted arylene group or a group of the formulae

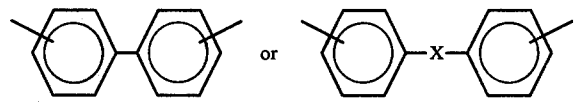

in which X denotes the bridge member —O—, —S—, —S—S—, —SO$_2$—, —CH$_2$—, —CO— or

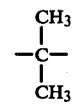

and the substituents on the aryl or arylene groups Q are free from acid hydrogen atoms, in a simple, economical manner and in good to very good yields by reacting an amide-acid of the formula II

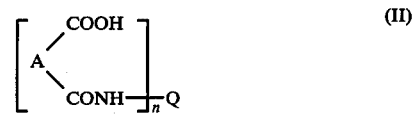

(II)

in which that stated under formula I applies in respect of A, Q and n, with ketene at a temperature of about −10° C. to +80° C. A preferably represents —CH=CH—.

The aryl or arylene groups represented by Q are, in particular, phenyl, 1- or 2-naphthyl, phenylene or naphthylene groups, especially the 1,3- or 1,4-phenylene group and 1,2-, 1,8- or 2,3-naphthylene group. Groups of this type can be unsubstituted or substituted. Possible substituents on the aryl or arylene groups Q which are free from acid hydrogen atoms are, for example, those which follow: halogen atoms, for example F, Cl, Br and I; alkyl groups, especially those with 1–8 carbon atoms; halogenoalkyl groups with 1–3 carbon atoms, such as the trifluoromethyl groups; alkylthio and N,N-dialkylamino groups, each with, preferably, 1–4 carbon atoms in the alkyl parts; alkoxy groups, above all those with 1–4 carbon atoms; phenoxy groups; alkoxycarbonyl and alkanoyl groups with, preferably, 2–5 carbon atoms, such as the methoxycarbonyl, ethoxycarbonyl and n-butoxycarbonyl group and the acetyl and propionyl group; phenylsulphonyl and alkylsulphonyl groups, the latter preferably containing 1–4 carbon atoms; and cyano and nitro groups. Aryl and arylene groups Q can contain 1 to 3, and preferably 1 or 2, substituents of this type. When n=1, Q preferably represents the 1- or 2-naphthyl group or a phenyl group which is substituted by one or two halogen atoms, especially chlorine atoms, one or two alkyl groups, each with 1–4, and especially 1 or 2, carbon atoms in the alkyl parts, or a trifluoromethyl, nitro or cyano group. When n=1, Q particularly preferentially denotes an unsubstituted phenyl group.

If n denotes the number 2, Q preferably represents the 1,3-phenylene group or 4,4'-diphenyl ether group, but above all the 4,4'-diphenylmethane group.

If the group Q has highly electronegative substituents, such as halogen atoms or nitro, cyano, alkyl or phenylsulphonyl groups, it is possible, depending on the position of these substituents on the radical Q, for relatively small or relatively large amounts of the corresponding imides of the formula Ia also to be formed, in addition to the iso-imides of the formula I, by the process according to the invention. The group Q therefore preferably has at most 2 of the highly electronegative substituents mentioned.

The reaction according to the invention is advantageously carried out in the presence of an organic solvent which is inert under the reaction conditions. Examples of suitable solvents are optionally chlorinated aromatic hydrocarbons, such as benzene, toluene, xylenes and chlorobenzene, chlorinated aliphatic hydrocarbons, such as chloroform, methylene chloride and 1,2-dichloroethane, aliphatic and cycloaliphatic ketones, such as acetone, methyl ethyl ketone and cyclohexanone, and also aliphatic and cyclic ethers, such as diethyl ether and dioxane. Particularly preferentially, the reaction is carried out in acetic anhydride, on the one hand because particularly high yields are achieved by this means and on the other hand because the acetic anhydride formed during the reaction with the ketene can, after distillation, be re-used for further reactions.

The amide-acids of the formula II are known or can be manufactured according to methods which are in themselves known, for example by reacting maleic anhydride or phthalic anhydride with monoamines or diamines of the formula H$_2$N—Q or H$_2$N—Q—NH$_2$ respectively.

The amide-acids of the formula II and ketene are preferably employed in a stoichiometric amount, that is to say when n=1, the amide-acid of the formula II and ketene are preferably employed in a molar ratio of 1:2, whilst when n=2, the molar ratio of the amide-acid of the formula II to ketene is advantageously 1:4. However, it is also possible to use a small excess of one or other of the reactants, for example to use an up to about 10% strength molar excess of the amide-acid of the formula II or ketene.

The acetic anhydride formed during the reaction can, as already mentioned, be recovered in a very simple manner by means of distillation and optionally re-used for further reactions.

The preferred reaction temperatures are between about 0° and +60° C. After the reaction has ended, the iso-imides of the formula I, or the mixtures of iso-imides of the formula I and imides of the formula Ia, can be isolated, and optionally purified, in a manner which is in itself known, for example by filtration, distillation and/or evaporation and subsequent washing with sodium bicarbonate solution and water or recrystallisation from suitable solvents, such as toluene, cyclohexane, acetone and methyl ethyl ketone.

Iso-imides which can be manufactured by the process according to the invention are in themselves known. N-substituted isomaleimides and N,N'-disubstituted bis-isomaleimides or bis-isophthalimides can be reacted with diamines, for example by the methods described in U.S. Pat. Nos. 2,980,701, 2,995,577, 2,998,429, 3,035,065 and 3,144,435 and Journal of Polymer Science: Polymer Chemistry Edition, 13, 1,691–1,698 (1975), to give linear polymers. N-substituted isophthalimides are used, for example, as intermediate products for the manufacture of pharmaceuticals [compare, for example, J. Med. Chem., 10, 982 (1967)]. Iso-imides of the formula I, wherein A represents the group —CH=CH—, can also be used as fungicides or defoliating agents.

Finally, the iso-imides of the formula I manufactured according to the invention can also be isomerised in a manner which is in itself known to the corresponding imides of the formula Ia, for example by treating them with catalytic amounts of an alkali metal salt or ammonium salt of lower fatty acids, such as sodium acetate (see, for example, U.S. Pat. No. 2,980,694). The imides of the formula Ia, in turn, are used, inter alia, as insecticides and/or for the manufacture of polymers.

EXAMPLE 1

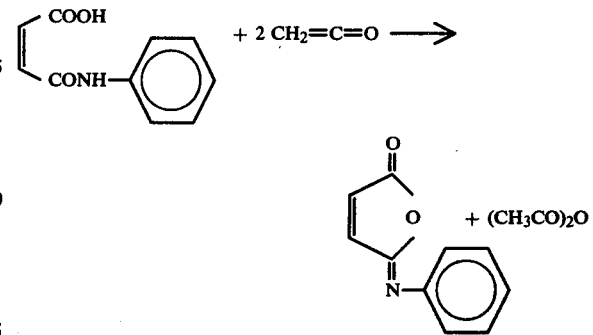

19.2 g (0.1 mol) of N-phenylmaleamic acid are suspended in 100 ml of acetic anhydride. Using a heating bath, the suspension is warmed to 45° C., whilst stirring, the heating bath is then removed and about 0.2 mol of ketene are passed into the suspension. The temperature then rises to 50°–52° C. and a clear yellow solution forms. This solution is concentrated in a rotary evaporator. The residual yellow oil is poured onto ice water. The precipitate hereupon formed is filtered off, washed with saturated sodium bicarbonate solution and water and dried in vacuo over phosphorus pentoxide. This gives 16.0 g (92% of theory) of N-phenyl-isomaleimide; melting point 58°–61° C.

IR spectrum (CHCl$_3$): λ$_{max}$. inter alia 5.55/5.95μ. Analysis for C$_{10}$H$_7$NO$_2$ (molecular weight 173.17):

calculated: C, 69.36%; H, 4.08%; N, 8.09%; found: C, 69.37%; H, 4.24%; N, 8.04%.

The acetic anhydride recovered when the solution is concentrated can be re-used after distillation.

EXAMPLE 2

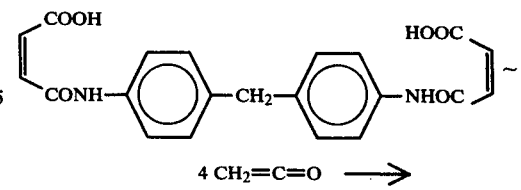

-continued

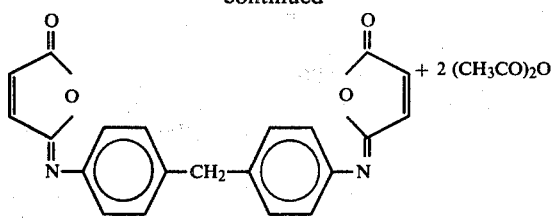

80 g (0.2 mol) of N,N'-4,4'-diphenylmethane-bis-maleamic acid are suspended in 600 ml of acetic anhydride, the suspension is heated to 45° C., whilst stirring, and 0.8 mol of ketene are passed in without heating. The temperature then rises to 49°–50° C. An almost clear yellow-orange solution forms and this is filtered whilst it is still warm. The filtrate is concentrated in a rotary evaporator to about ⅓ of its original volume. The reaction product is then allowed to crystallise out in a refrigerator, the mixture is filtered and the residue is washed with saturated sodium bicarbonate solution and water. The resulting yellow crystals are dried in vacuo. This gives 56.7 g (79% of theory) of N,N'-4,4'-diphenylmethane-bis-isomaleimide; melting point 154°–155° C.

IR spectrum (CHCl$_3$): $\lambda_{max}$. inter alia 5.55/5.95µ.

Analysis for C$_{21}$H$_{14}$N$_2$O$_4$ (molecular weight 358.35): calculated: C, 70.39%; H, 3.94%; N, 7.82%; found: C, 70.34%; H, 3.95%; N, 7.65%.

The acetic anhydride recovered can be re-used after distillation.

EXAMPLE 3

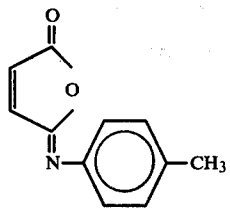

Analogously to the process described in Example 1, 10.3 g (0.05 mol) of N-p-tolylmaleamic acid in 75 ml of acetic anhydride and 0.1 mol of ketene give 8.6 (92% of theory) of N-p-tolyl-isomaleimide with a melting point of 71°–73° C.

IR spectrum (CHCl$_3$): $\lambda_{max}$ inter alia 5.59/5.99µ.

Analysis for C$_{11}$H$_9$NO$_2$ (molecular weight 187.20): calculated: C, 70.58%; H, 4.85%; N, 7.48%; found: C, 70.67%; H, 4.77%; N, 7.53%.

EXAMPLE 4

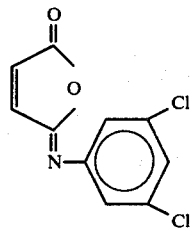

Analogously to the process described in Example 1, 26.0 g (0.1 mol) of N-3,5-dichlorophenylmaleamide in 200 ml of acetic anhydride and 0.2 mol of ketene give 23.1 g (95% of theory) of N-3,5-dichlorophenyl-isomaleimide; melting point 82°–85° C.

IR spectrum (Nujol): $\lambda_{max}$. inter alia 5.55/5.80µ.

Analysis for C$_{10}$H$_5$Cl$_2$NO$_2$ (molecular weight 242.06): calculated: C, 49.62%; H, 2.08%; N, 5.79%; Cl, 29.29%; found: C, 49.26%; H, 2.21%; N, 5.67%; Cl, 28.75%.

EXAMPLE 5

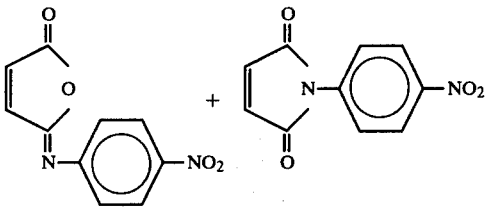

Analogously to the procedure described in Example 1, about 0.08 mol of ketene are introduced into a suspension of 10.0 g (0.042 mol) of N-p-nitrophenylmaleamic acid in 75 ml of acetic anhydride. This gives 8.6 g (94% of theory) of the reaction product which, according to the IR spectrum and NMR spectrum, consists of a mixture of N-p-nitrophenyl-maleimide and N-p-nitrophenyl-isomaleimide; melting point 97°–150° C.

IR spectrum (CHCl$_3$): $\lambda_{max}$. inter alia 5.48/5.54/5.90µ (iso-imide); 5.78µ (imide).

Analysis for C$_{10}$H$_6$N$_2$O$_4$ (molecular weight 218.17): calculated: C, 55.05%; H, 2.77%; N, 12.84%; found: C, 54.75%; H, 2.78%; N, 12.89%.

EXAMPLE 6

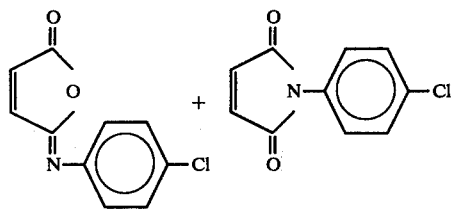

Analogously to the procedure described in Example 1, 0.6 mol of ketene is passed into a suspension of 67.5 g (0.3 mol) of N-p-chlorophenylmaleamic acid in 600 ml of acetic anhydride. This gives 59.4 g (95% of theory) of the reaction product which, according to the IR spectrum, consists in the main of N-p-chlorophenyl-isomaleimide and in small proportions of N-p-chlorophenyl-maleimide; melting point 85°–95° C.

IR spectrum (CHCl$_3$): $\lambda_{max}$. inter alia 5.55/5.95µ (iso-imide); 5.70µ (imide).

Analysis for C$_{10}$H$_6$ClNO$_2$ (molecular weight 207.62): calculated: C, 57.85%; H, 2.91%; N, 6.75%; Cl, 17.08%; found: C, 57.63%; H, 3.02%; N, 6.92%; Cl, 17.03%.

EXAMPLE 7

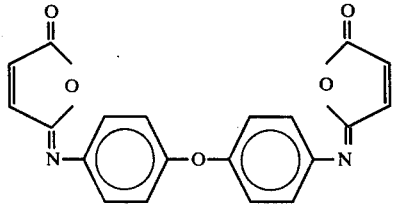

40 g (0.1 mol) of N,N'-(4,4'-diphenyl ether)-bis-maleamic acid are suspended in 400 ml of acetic anhydride. The suspension is warmed to 45° C., whilst stirring. Subsequently, the heating is removed and 0.4 mol of ketene is passed in. The temperature then rises to 52° C. An orange-yellow suspension is obtained and this is filtered whilst still warm (conversion 88%; 5 g of residue consisting of unconverted bis-maleamic acid). The filtrate is concentrated to dryness in a rotary evaporator at a bath temperature of 60° C.

The residue is suspended in 100 ml of diethyl ether, the suspension is filtered and the product is rinsed with 20 ml of diethyl ether and dried in vacuo over potassium hydroxide. This gives 25.5 g (80% of theory, based on an 88% conversion) of orange-yellow N,N'-(4,4'-diphenyl ether)-bis-isomaleimide; melting point 155°–159° C.

IR spectrum (CHCl$_3$): $\lambda_{max}$. inter alia 5.55/5.95μ.

Analysis for C$_{20}$H$_{12}$N$_2$O$_5$ (molecular weight 360.33): calculated: C, 66.67%; H, 3.36%; N, 7.78%; found: C, 66.14%; H, 3.51%; N, 7.69%.

EXAMPLE 8

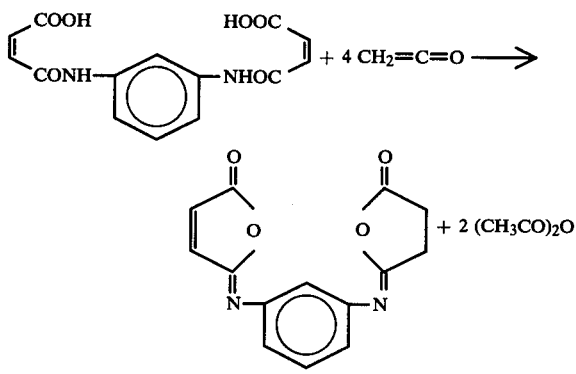

Analogously to the procedure described in Example 7, 30.4 g (0.1 mol) of N,N'-1,3-phenylene-bis-maleamic acid in 400 ml of acetic anhydride and 0.4 mol of ketene give 22.0 g (82% theory) of N,N'-1,3-phenylene-bis-isomaleimide; melting point 172°–177° C.

IR spectrum (CHCl$_3$): $\lambda_{max}$. inter alia 5.55/5.95μ.

Analysis for C$_{14}$H$_8$N$_2$O$_4$ (molecular weight 268.23): calculated: C, 62.69%; H, 3.01%; N, 10.44%; found: C, 62.29%; H, 3.02%; N, 10.60%.

EXAMPLE 9

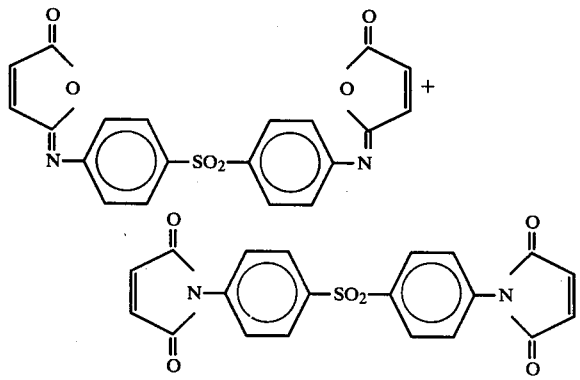

40.5 g (0.091 mol) of N,N'-4,4'-diphenylsulphone-bis-maleamic acid are suspended in 400 ml of acetic anhydride. Using a heating bath, the resulting suspension is warmed to 45° C., whilst stirring, the heating bath is then removed and 0.4 mol of ketene is passed into the suspension. The temperature then rises to 48° C. Unconverted amide-acid (0.500 g, that is to say 99% conversion) is removed by filtering off and the filtrate is evaporated in a rotary evaporator. The yellow solid residue is suspended in saturated sodium bicarbonate solution, the suspension is filtered and the product is rinsed with water. After drying in vacuo at 20°–25° C., this gives 34.8 g (95% of theory) of a product which, according to the IR spectrum, consists in the main of N,N'-4,4'-diphenylsulphone-bis-maleimide and in smaller proportions of N,N'-4,4'-diphenylsulphone-bis-isomaleimide; melting point 195°–205° C.

IR spectrum (CHCl$_3$): $\lambda_{max}$. inter alia 5.55/5.90μ (iso-imide); 5.80μ (imide).

Analysis for C$_{20}$H$_{12}$H$_2$O$_6$S (molecular weight 408.38): calculated: C, 58.82%; H, 2.96%; N, 6.86%; S, 7.85%; found: C. 58.62%; H. 3.18%; N. 6.66%; S. 7.76%.

EXAMPLE 10

40 g (0.1 mol) of N,N'-4,4'-diphenylmethane-bis-maleamic acid are suspended in 150 ml of acetone. 0.4 mol of ketene is passed in at 35° C. The resulting yellow suspension is filtered (15.2 g of residue of consisting unconverted bis-maleamic acid, conversion=62%), the filtrate is poured onto ice water and the precipitate is filtered off, washed with saturated sodium bicarbonate solution and finally dried in vacuo at 20°–25° C. This gives 20.8 g (92% of theory, based on a 62% conversion) of N,N'-4,4'-diphenylmethane-bis-isomaleimide.

IR spectrum (CHCl$_3$): $\lambda_{max}$. inter alia 5.55/5.95μ

EXAMPLE 11

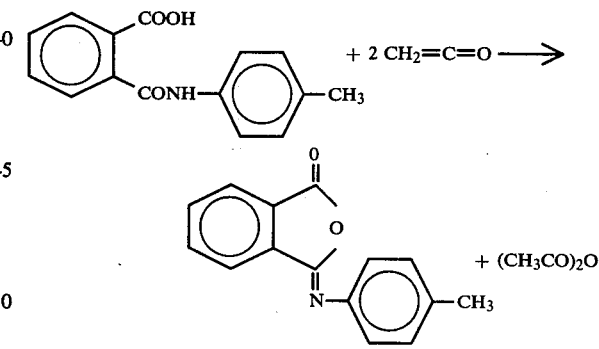

25.6 g (0.1 mol) of N-p-tolyl-phthalamic acid are suspended in 250 ml of acetic anhydride at 20°–25° C. 0.2 mol of ketene is then passed in and the temperature rises to 33° C. A clear, pale yellowish solution forms and is concentrated in vacuo in a rotary evaporator (bath temperature 60° C.) and the residue is suspended in saturated sodium bicarbonate solution, the suspension is filtered and the product is washed with water. After drying in vacuo at 40° C., this gives 21.0 g (88% of theory) of N-p-tolyl-isophthalimide; melting point 116°–118° C.

IR spectrum (CHCl$_3$): $\lambda_{max}$. inter alia 5.55/5.85μ.

Analysis for C$_{15}$H$_{11}$NO$_2$ (molecular weight 237.26): calculated: C, 75.94%; H, 4.67%; N, 5.91%; found: C, 75.64%; H, 4.65%; N, 6.01%.

EXAMPLE 12

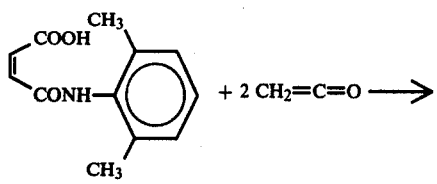

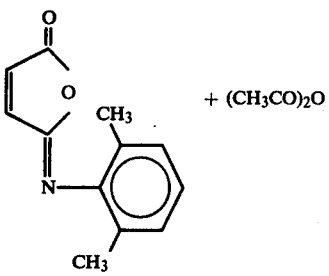

100.1 g (0.457 mol) of N-(2,6-dimethylphenyl)-maleamic acid are suspended in 750 ml of acetic anhydride. Using a heating bath, the suspension is warmed to 30° C., the heating bath is then removed and about 0.9 mol of ketone is passed into the suspension, whilst stirring. The temperature then rises to 40° C. and a yellow homogeneous solution forms. The acetic anhydride is removed in a rotary evaporator, the residue is taken up in benzene and the solution is washed with saturated sodium bicarbonate solution and water, dried and evaporated in a rotary evaporator. This gives 90.4 g (98% of theory) of deep yellow crystalline N-(2,6-dimethylphenyl)-isomaleimide with a melting point of 60°–62° C.

IR spectrum (CHCl$_3$): $\lambda_{max}$. inter alia 5.50/5.55/5.90μ.

Analysis for C$_{12}$H$_{11}$NO$_2$ (molecular weight 201.23):

calculated: C, 71.63%; H, 5.51%; N, 6.96%; O, 15.90%; found: C, 71.45%; H, 5.59%; N, 7.20%; O, 15.98%.

What is claimed is:

1. Process for the manufacture of an iso-imide of the formula I

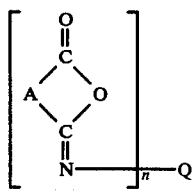

or a mixture of an iso-imide of the formula I and an imide of the formula Ia

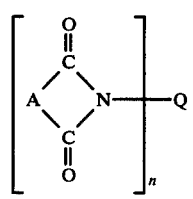

in which A represents —CH=CH— or

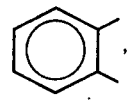

n represents the number 1 or 2 and, when n=1, Q represents a phenyl, 1-naphthyl or 2-naphthyl group; and, when n=2, represents a phenylene or naphthylene group; or said phenyl, naphthyl, phenylene or naphthylene group substituted by 1 or 2 moieties which are free from acid hydrogen atoms and which are selected from the group consisting of halogen, alkyl with 1 to 8 carbon atoms, halogenoalkyl with 1 to 3 carbon atoms, alkylthio with 1 to 4 carbon atoms, N,N-dialkylamino with 1 to 4 carbon atoms, alkoxy with 1 to 4 carbon atoms, phenoxy, alkoxycarbonyl with 2 to 5 carbon atoms, alkanoyl with 2 to 5 carbon atoms, phenylsulphonyl, alkylsulphonyl with 1 to 4 carbon atoms, cyano and nitro; or when n=2, Q also represents a group of the formulae

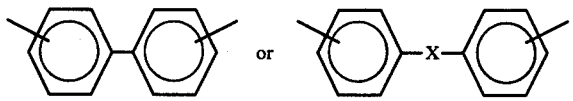

in which X denotes the bridge member —O—, —S—, —S—S, —SO$_2$—, —CH$_2$—, —CO— or

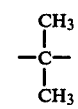

which process comprises reacting an amide-acid of the formula II

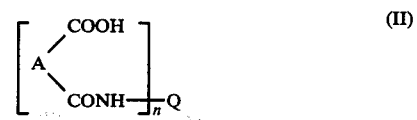

in which that stated under formula I applies in respect of A, Q and n, with ketene at a temperature of about −10° C. to +80° C.

2. Process according to claim 1, wherein an amide-acid of the formula II in which A represents —CH=CH— is used.

3. Process according to claim 1, wherein an amide-acid of the formula II in which n represents the number 1 and Q represents the 1- or 2-naphthyl group, or a phenyl group which is substituted by 1 or 2 halogen atoms, one or 2 alkyl groups, each with 1–4, carbon atoms in the alkyl parts, or a trifluoromethyl, nitro or cyano group, is used.

4. Process according to claim 1, wherein an amide-acid of the formula II in which A represents —CH=CH—, n represents the number 1 and Q represents an unsubstituted phenyl group is used.

5. Process according to claim 1, wherein an amide-acid of the formula II in which A represents —CH=CH—, n represents the number 2 and Q represents the 1,3-phenylene, 4,4'-diphenyl ether group or 4,4'-diphenyl methane group is used.

6. Process according to claim 1, wherein the reaction is carried out in the presence of an organic solvent which is inert under the reaction conditions.

7. Process according to claim 1, wherein the reaction is carried out in the presence of acetic anhydride.

8. Process according to claim 1, wherein the reaction is carried out at a temperature between about 0° and 60° C.

9. Process according to claim 5 wherein Q is the 4,4' diphenylmethane group.

* * * * *